United States Patent [19]

Polski

[11] Patent Number: 5,066,289
[45] Date of Patent: Nov. 19, 1991

[54] RELEASE TREATED NON-WOVEN FASTENING TAPE PROTECTOR

[75] Inventor: Stephen P. Polski, Shoreview, Minn.

[73] Assignee: Minnesota Mining and Manufacturing Company, St. Paul, Minn.

[21] Appl. No.: 506,912

[22] Filed: Apr. 9, 1990

[51] Int. Cl.$^5$ .................. A61F 13/15; A61F 13/20
[52] U.S. Cl. .................. 604/389; 604/390; 604/391; 604/385.1
[58] Field of Search .......... 604/385.1, 385.2, 386, 604/387, 389, 390, 391

[56] References Cited

U.S. PATENT DOCUMENTS

| | | | |
|---|---|---|---|
| 3,967,622 | 7/1976 | Cepuritis | 604/390 |
| 4,034,752 | 7/1977 | Tritsch | 604/390 |
| 4,194,507 | 3/1980 | Ness et al. | 128/287 |
| 4,699,622 | 10/1987 | Toussant et al. | 604/389 |
| 4,871,611 | 10/1989 | LeBel | 428/266 |
| 4,911,702 | 3/1990 | O'Leary et al. | 604/389 |

FOREIGN PATENT DOCUMENTS 2151460 7/1985 United Kingdom ............ 604/385.1

*Primary Examiner*—Randall L. Green
*Assistant Examiner*—Paul Prebilic
*Attorney, Agent, or Firm*—Gary L. Griswold; roger R. Tamte; William J. Bond

[57] ABSTRACT

There is provided an improved two-point diaper closure system comprised of inner mechanical and outer adhesive fastening means. The outer adhesive fastening means is used in conjuction with a release treated foraminous tab located on the diaper top sheet.

8 Claims, 1 Drawing Sheet

U.S. Patent    Nov. 19, 1991    5,066,289
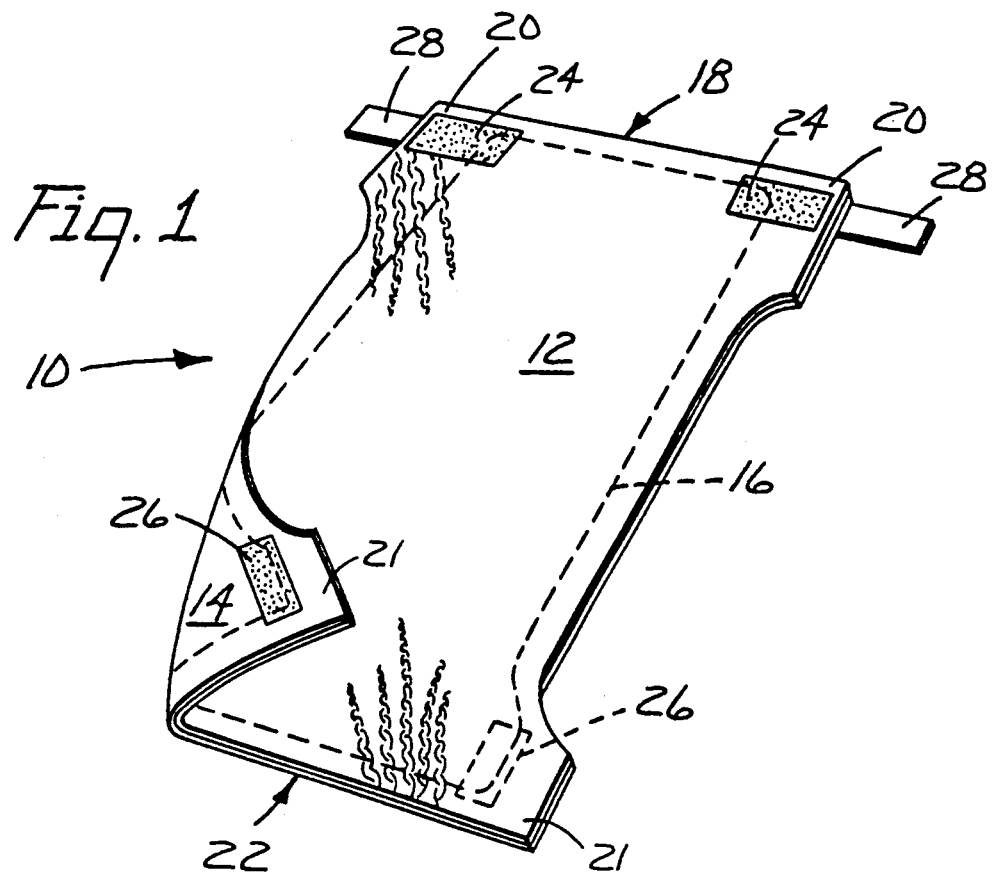
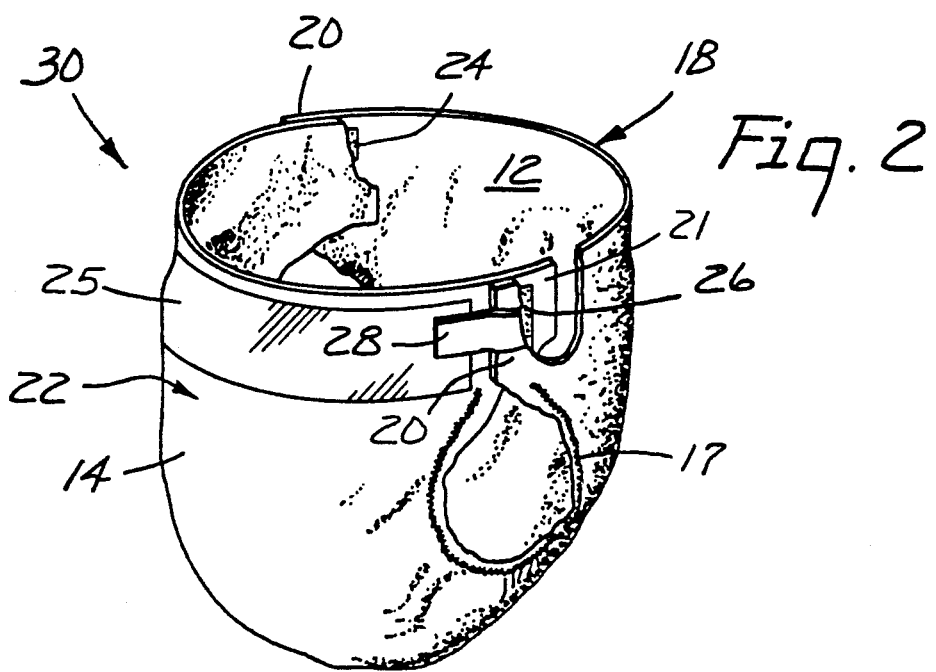

RELEASE TREATED NON-WOVEN FASTENING TAPE PROTECTOR

BACKGROUND AND FIELD OF THE INVENTION

This invention is concerned with disposable diaper adhesive and non-adhesive type closure systems and more particularly to an improved side closure system for disposable diapers comprised of two separate fastening systems, one each of the adhesive and of the nonadhesive type.

Disposable diapers and related articles are well known. A conventional type of diaper system used by both infants and incontinent adults is comprised of an absorbent core encased between a liquid permeable "top sheet" (the user contacting face) and a liquid impermeable "back sheet" (the outer shell portion), which composite encircles the wearer's waist in association with closure systems. These closure systems are most frequently located so that they join front and rear ends or panels of the diaper. These closure systems are most commonly located at either side of the wearer. In order to improve the fit of these diapers and prevent leakage, the side edge portions of the diapers are frequently elasticized which, when the diaper is joined by the side closure systems, provide elasticized leg openings which grip the wearer's thighs.

Conventional diaper closure systems are discussed in U.S. Pat. No. 4,699,622 (Toussant et al.). Toussant et al. was concerned with the problem of diapers shifting on the wearer when used. More specifically, Toussant et al. stated this problem as where "overlapping front and back waist portions were subjected to forces which tend to cause the front and back waist portion to assume a position relative to each other which is different from the position they assume when a diaper is initially fitted to the wearer."

Toussant et al.'s proposed solution to this problem is a two-point closure system comprised of a conventional type "outer fastening means", which fixes overlapping corners of the front and rear diaper panels to each other. This outer fastening is preferably done with an adhesive fastening tab that will releasably attach to the diaper "backsheet", preferably on a front panel located at the waist engaging portion or area of the diaper. In addition to this outer fastening means, Toussant et al. proposes the use of an "inner fastening means" to prevent shifting of the overlapping corners of the diaper, each with respect to the other, from wearer movement and forces from the elasticized portions of the diaper. Specifically, an inner fastening means is proposed which would resist tensile and peel forces, encountered by the diaper closure system when worn, to prevent separation of the overlapping corner portions. Preferably, the inner fastening means is disclosed as a mechanical type fastener, i.e., a fastener of the type that carries a plurality of projecting members such as hooks which engage with another substrate, such as one that carries loops or fibers into which the projecting members engage. The mechanical fastener is fixed to the corner at the front panel portion of the diaper and is capable of entangling with, e.g., fibrous material typically used as the porous top sheet. The preferred material disclosed is that marketed by 3M Company, St. Paul, MN under the trade name SJ 3492.

A problem with the closure system proposed by Toussant et al., resides in the fact that the outer fastening means contemplated as preferred is a conventional adhesive type closure system comprised of a fastening tab. Most conventional adhesive fastening tabs are used in combination with a release coated tape located on the top sheet of the diaper where the free end of the fastening tab is placed when not in use. When the fastening tab is used, it is removed from the release tape and attached to the front panel of the back sheet of the diaper. The principal problem with this system resides in that these release coated tapes are generally located at one of the most likely areas for the Toussant et al. inner fastening means to attach to the top sheet. This is a problem in that a release coated tape conventionally is a surface treated polyolefin tape resistant to attachment by both conventional adhesives and mechanical fastening means, such as disclosed in Toussant et al. These release coated tapes will therefore seriously interfere with attachment of the Toussant et al. mechanical fastening means to the diaper top sheet, particularly where the mechanical fastening means is of a size and shape on the order of the size and shape of the release coated tape.

SUMMARY OF THE INVENTION

In accordance with the invention, a disposable diaper is provided such as disclosed in Toussant et al., namely, an absorbent inner core sandwiched between a liquid permeable top sheet and a liquid impervious back sheet. The side portions of the diaper are made of elastic so as to engage the wearer's thighs.

The disposable diaper of the present invention is provided with an outer fastening means comprised of at least an adhesive fastening tab and an associate release tab and is further provided with an inner fastening means comprising a mechanical fastener, such as disclosed in Toussant et al., adapted to engage at least the top sheet of the diaper. The improvement lies in providing a novel release tab on the diaper top sheet comprised of a release treated non-woven web so as to provide for an uninterrupted engaging surface for the mechanical fastener on the diaper top sheet.

BRIEF DESCRIPTION OF THE DRAWINGS

FIG. 1 is a schematic view of a disposable diaper from the top sheet side;

FIG. 2 is a schematic view of a disposable diaper similar to that of FIG. 1 as it would appear while being worn.

DESCRIPTION OF THE PREFERRED EMBODIMENT

Referring to the drawings, there is shown a preferred embodiment of the present invention used in a disposable diaper, such as would be worn by an infant or an incontinent adult. The disposable diaper 10 shown in FIG. 1 would conventionally be a three-layer composite including a liquid permeable, user contacting top sheet 12, a liquid-impervious outer shell or back sheet 14 and an absorbent layer 16. At the back 18 of the diaper are corners 20 that overlap with corresponding corners 21 at the front panel 22 of the diaper when the diaper is worn. On the top sheet side of the diaper at each of the corners 20 is located a release treated, non-woven release tab 24 and on the outer shell or backsheet 14 at the front corners 21 of the diaper 10 are mechanical type fasteners 26.

Diaper 10 is wrapped around a person to assume the shape of the diaper 30 shown in FIG. 2. In the arrangement shown in FIG. 2, each of the release treated non-woven tabs 24, at the back corners 20, will be able to contact and engage with one of the mechanical fasteners 26 at the front corners 21 of the diaper 10.

For most conventional designs, the fastening tabs 28 are located at the back sheet 18 of the diaper 10. During non-use the tabs 28 would be located on the non-woven release treated tabs 24. When in use, the fastening tabs 28 would be removed from the release treated non-woven tabs 24 and attached to a front panel 22 of the diaper back sheet 18. Generally, the diaper front panel 22 is provided with a landing or frontal strip 25 which reinforces the diaper at the waist portion of the front diaper panel 22, allowing removal and replacement of the fastening tab as necessary. The side edge portions of the diaper are also provided with elastizing elements 17, as shown in FIG. 2, which provide for engaging the leg or thigh of the wearer when the diaper is in use. The diaper can be constructed by any conventional means as is disclosed in Toussant et al.

Conventionally, the top sheet 12 of the diaper is a soft non-irritating fabric to prevent irritation of the wearer's skin. Further, the top sheet 12 is made liquid permeable to permit passage of liquids to the absorbent layer 16. Top sheets are generally fibrous woven or non-woven sheets formed of, e.g., natural fibers, such as cellulose, or synthetic fibers of polyester, polyethylene, or polypropylene or a combination thereof. Further, the fibers may or may not be treated depending upon the surface characteristics of the fiber and the desired properties of the top sheet. Other materials capable of passing moisture to the absorbent inner layer are also possible, such as a formed film or foam, e.g., a reticulated foam, as is known in the art.

The topsheet 12 can be formed by any suitable method including weaving, non-woven manufacturing such as spinbonding, carding, etc.

Fastening tab 28 will generally be permanently fixed to back sheet 14 at corners 20, although other placements are possible, by any suitable method. Generally, pressure-sensitive adhesives are preferred to fix the tab 28 to the back sheet 14. However, in addition to using pressure-sensitive adhesives, the fastening tabs 28 can be directly heat sealed to the back sheet 14 or adhered using a heat or solvent activated adhesive, depending upon the nature of the back sheet. The opposite end of the fastening tab 28 will be releasably attached to the release tabs 24 when not in use and removed by the user for placement on, e.g., the frontal strip 25 on the back sheet 14. This will cause overlap of corners 20 and 21. Generally, the user or free end of the fastening tab 28 is provided with a releasable pressure-sensitive adhesive.

With the above described placement of the fastening tab 28, the release tab 24 will be provided on the top sheet 12 of the diaper at a location such that the user end of the fastening tab 28 can be folded over onto the release tab 24. In accordance with the invention, the size of the release tab 24 is not critical, however, generally for economy it will be only of a size sufficient to cover the user end of the fastening tab 28 when such is folded over onto the release tab.

In accordance with the above described preferred embodiment, the inner fastening means is provided on the back sheet 14 of the diaper at corners 21, which inner fastening means comprises a mechanical fastening means 26, which adheres to a mechanical fastening means 26 is provided, in accordance with the teachings of Toussant et al., to resist shear forces, which may cause the overlapping corners 20 and 21 to shift relative to each other when the diaper or incontinence article is worn. The inner fastening means 26 is preferably a discrete mechanical fastener capable of mechanically engaging with a fibrous substrate such as the top sheet 12. Although the mechanical fastening means 26 can be of any suitable size and shape, it is preferably only of a size sufficient to provide sufficient resistance to the shear and the elastic forces which may cause the corners 20 and 21 to shift relative to each other.

Release tab 24 shown is located on the top sheet side of corner 20. The top sheet face of corner 20 will overlap with the back sheet face of corner 21 when the diaper is assembled as shown in FIG. 2. To ensure that the mechanical fastening means 26 has an engagable surface over the entire engagement area (e.g., the top sheet face of overlapping corner 20), the top sheet 12 of the present invention is provided with the novel release tab comprised of a surface treated foraminous substrate, such as a non-woven web or a looped woven web, which permits penetration and attachment of the mechanical fastening means 26. The foraminous substrate, preferably a non-woven material, can be formed of any suitable material including natural fibers such as cellulose fibers, cotton fibers, wool fibers, wood-pulp, or synthetic fibers such as viscose fibers, polypropylene, polyethylene, nylon, acrylic, polyester or like fibers, or combinations and/or blends of the above fibers. To form the foraminous substrate, any suitable non-woven manufacturing technique can be used including, e.g., carding with point bonding, or spinbonding. The non-woven should have a basis weight that gives it sufficient integrity to withstand release coating and application to the, e.g., diaper. The basis weight, however, should not be so high that the mechanical fastener elements cannot easily penetrate the release tab. Generally, a basis weight of from 20–55 gm/yd$^2$ (23.9–65.8 gm/m$^2$) is functionable. However, lower basis weights are still functional, particularly when the release tab is laminated to an, e.g., non-woven or foraminous substrate. A non-woven basis weight of 20 to 25 gm/yd$^2$ (23.9–29.9 gm/m$^2$) is preferred for most applications. From a manufacturing perspective, a dry tensile strength of at least approximately 300 gm/cm in the machine direction is desirable. Too low of a tensile strength will make the non-woven difficult to handle and convert to a release tab.

The release treatment on the release tab can be by any conventional composition known for this purpose and applied by any known method including fabric impregnation, saturation, gravure application, etc. Preferred agents include silicone containing agents or compounds such as radiation curable polysiloxanes (disclosed in Great Britain Patent Application 2,183,174) or reactive silicones. Other suitable release agents are disclosed, for example, in Ness et al, U.S. Pat. No. 4,194,507.

In order to ensure adequate penetration of the mechanical fastening elements, by the mechanical fastening means 26, preferably release tab 24 is attached intermittently over its back surface to the top sheet 12. This can be accomplished by means such as spot welding (e.g., ultrasonic welding) intermittently applied, spot adhesion or the like. This intermittent attachment prevents extensive interference with penetration of the engaging elements on the surface of the mechanical fastening means 26.

EXAMPLE 1

A spun bond polypropylene non-woven fabric, basis weight 60 gm/m$^2$ (2.0 oz./yard$^2$), purchased from James River Corporation was saturated with 3.0% solid solution of a reactive silicone, Syl Off TM 294 available from Dow Corning of Midland, MI. Excess solution was removed and the sample dried and cured at 150° F. (66° C.) for 5 minutes in a forced air oven. The thus-formed sample was tested for 90° peel in conjunction with a refastenable fastening tape, KR-2342 available from Minnesota Mining and Manufacturing Company. The tape was subjected to a 4.5 pound (2.04 kg) roll-down and removed at 12 inches (30.5 cm) per minute on an Instron TM (variation of PSTC (Pressure Sensitive Tape Council)-5). The results yield a 90° peel value of 2.8 N/25 mm (275 grams per inch) using a sample size of 52 replications. By comparison, a standard release tape KR-8150 available from Minnesota Mining and Manufacturing Co. (3M) tested identically yielded a 90° peel value of 3.1 N/25 mm (300 grams per inch).

Samples of the non-woven sheet were then attached to a standard non-woven top sheet (the above James River non-woven fabric) by sonic welding using a horn pressure of 37 psi (21600 gm/cm$^2$) at 100% tuning, 1 second weld time, 1 second hold time and at a amplitude of 57.

The release treatment of the non-woven release tape substrate did not interfere with the sonic bonding, and when tested with a mechanical fastener provided a surface which the mechanical fastener could penetrate and attach. This sample of release treated non-woven substrate was tested in accordance with the procedure outlined in U.S. Pat. No. 4,699,622 using a mechanical fastening material marketed by 3M Company, St. Paul, MI, SJ 3492. On a glass plated sled was placed a ⅛ inch (0.3×175 centimeters) width urethane foam, flanked by two 1 inch (2.54 centimeters) pieces of double coated tape. The treated non-woven substrate and then an untreated non-woven substrate were placed on the double coated tape. The non-woven substrate was placed so that its machine direction was parallel with the direction of sled movement. A 1×½ inch (2.54×1.27 cm) sample of the mechanical fastener, attached to a leader was placed on the non-woven, over which was placed a weight of about 17 grams/cm$^2$. The sled was then moved at a constant rate of 12 inches/min (30.5 cm/min). The leader was attached to a force tester which measured the force from the leader when the mechanical fastener started moving relative to the non-woven material. For the untreated non-woven, this force was 709 grams, while for the treated non-woven the force was 708 grams.

From this, it is clear that the treated non-woven will perform on a par with conventional untreated non-woven materials. As for U.S. Pat. No. 4,699,622, the shear force may be applied and measured by any known machine or arrangement known to those of skill in the testing field.

Other embodiments of the invention will be apparent to those skilled in the art from consideration of the specification or practice of the invention disclosed herein. It is intended that the specifications and examples be considered as exemplary, with the true scope and spirit of the invention being indicated by the following claims.

I claim:

1. A two-point side fastening diaper comprising a first fastening means with at least an adhesive fastening tab means, and an associated adhesive release tab means both disposed at at least one corner of a first end of the diaper such that the fastening tab means can be folded over into engagement with the release tab means, said adhesive release tab comprising a foraminous substrate treated with a release agent, a second fastening means comprising a mechanical fastening element located at a corner at a second end of said diaper, wherein when said corners on the same side and different ends of said diaper are overlapped to close said diaper, said mechanical fastening element is capable of mechanically engaging said release tab.

2. The diaper of claim 1 wherein said release tab is intermittently sonically welded to a liquid permeable diaper top sheet face.

3. The diaper of claim 1 wherein said release tab is formed of a non-woven material.

4. The diaper of claim 1 wherein said release tab is treated with a silicon containing release agent.

5. The diaper of claim 1 wherein said first fastening means is located on a liquid impermeable back sheet at a first end of said diaper adapted to be positioned at the back side of an user and said second fastening means is located on said liquid impermeable back sheet at a second end of the diaper adapted to be positioned at the front side of a user.

6. The diaper of claim 5 wherein said second fastening means is located on the back sheet face of said diaper and said release tape is located on the top sheet face of said diaper.

7. A diaper comprising an outer shell, a liquid permeable non-woven topsheet which contacts the wearer, a non-woven release tab attached to said non-woven topsheet at a corner of said non-woven topsheet, and a diaper fastening tab adjacent the non-woven release tab to permit engagement therewith, said non-woven release tab comprising a non-woven substrate capable of engaging a mechanical fastener, which substrate has been treated with a release agent which resists permanent attachment to a pressure sensitive adhesive such as is used on a diaper fastening tab wherein the non-woven release tab is relatively soft and non-irritating to the wearer.

8. The diaper of claim 7 wherein said release tab is formed of a non-woven material.

* * * * *